US006455660B1

(12) United States Patent
Clutton et al.

(10) Patent No.: US 6,455,660 B1
(45) Date of Patent: Sep. 24, 2002

(54) HOMOPOLYMER OF ETHYLENE

(75) Inventors: Edward Quentin Clutton, Edinburgh; Philip Stephen Hope, Alva; Stephen Roy Partington, Walton-on-Thames; John Norman Reid Samson, Stirling, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/659,713

(22) Filed: Sep. 11, 2000

Related U.S. Application Data

(63) Continuation of application No. PCT/GB99/00713, filed on Mar. 10, 1999.

(30) Foreign Application Priority Data

| Mar. 12, 1998 | (GB) | 9805336 |
| Mar. 27, 1998 | (GB) | 9806661 |
| May 7, 1998 | (GB) | 9809598 |
| Oct. 23, 1998 | (GB) | 9823319 |

(51) Int. Cl.$^7$ ............................ C08F 110/02; C08F 4/70
(52) U.S. Cl. ................ 526/352; 526/133; 526/159; 526/131; 526/165; 526/172
(58) Field of Search ................ 526/352, 133, 526/159, 131, 165, 172

(56) References Cited

U.S. PATENT DOCUMENTS 5,955,555 A * 9/1999 Bennett .................. 526/133

FOREIGN PATENT DOCUMENTS

WO   WO 98/27124   6/1998

* cited by examiner

Primary Examiner—David W. Wu
Assistant Examiner—Caixia Lu
(74) Attorney, Agent, or Firm—Finnegan, Henderson, Farabow, Garrett and Dunner, L.L.P.

(57) ABSTRACT

A polyethylene having the following properties: an annealed density D/weight average molecular weight $M_w$ relationship defined by the equation $D > 1104.5 M_w^{-0.0116}$, and a Charpy Impact I/High Load Melt Index H relationship defined by the equation $I > 35.0 H^{-0.4}$. Also, a polyethylene film having the following properties: a density of at least 957 kg/m$^3$; a Dart Impact of at least 130 g; and a polydispersity of less than 12. Both may be made using a tridentate nitrogen-containing transition metal polymerization catalyst.

19 Claims, 4 Drawing Sheets

HOMOPOLYMER OF ETHYLENE

This application is a continuation of international application No. PCT/GB99/00713 filed Mar. 10, 1999.

FIELD OF THE INVENTION

The present invention relates to novel polyethylene compositions.

Many different grades of polyethylene are manufactured for different applications, and equally there is a wide variety of physical properties of polyethylene which are important in each case. Generally it is not just one property which is important for a particular application, but several: finding a polyethylene which possesses the right combination of those properties is the major objective of much research. For example, in pipe and moulding applications properties such as density, viscosity (i.e. melt flow rate), impact strength and rigidity are all important.

BACKGROUND

The use of certain transition metal compounds to polymerise 1-olefins, for example, ethylene, is well established in the prior art. Silica-supported chromium catalysts using the Phillips process have been known for several decades. The use of Ziegler-Natta catalysts, for example those catalysts produced by activating titanium halides with organometallic compounds such as triethylaluminium, is fundamental to many commercial processes for manufacturing polyolefins. In recent years the use of certain metallocene catalysts (for example biscyclopentadienylzirconiumdichloride activated with alumoxane) has provided catalysts with potentially high activity. These different catalyst systems provide polymeric products with a variety of properties.

Commodity polyethylenes are produced commercially in a variety of different types and grades. Homopolymerisation of ethylene with transition metal based catalysts leads to the production of so-called "high density" grades of polyethylene. These polymers have relatively high stiffness and are useful for making articles where inherent rigidity is required, such as pipe and moulded products.

WO98/27124, published after the earliest priority date of this invention, discloses that ethylene may be polymerized by contacting it with certain iron or cobalt complexes of selected 2,6-pyridinecarboxaldehydebis(imines) and 2,6-diacylpyridinebis(imines). There is no disclosure regarding the properties of polyethylene produced by such catalysts and because the polyethylene produced in those Examples where the molecular weight is higher than oligomeric mostly shows extremely broad molecular weight distributions, it would not have the range of properties considered in this application.

SUMMARY OF THE INVENTION

We have discovered a class of novel homopolymers of ethylene which have a combination of properties that make them particularly suitable for use in pipe, film and moulded products. Accordingly a first aspect of the invention provides a homopolymer of ethylene which has:

an annealed density D/weight average molecular weight $M_W$ relationship defined by the equation equation $D > 1104.5 M_W^{-0.0116}$; and either a Charpy Impact I/High Load Melt Index H relationship defined by the equation $I > 35.0 H^{-0.4}$, or a dynamic storage modulus G' of 2.9 or less.

Weight average molecular weight $M_W$ is measured by GPC. Annealed density is measured to specification ISO 1872-1:1993 using test method ISO 1183:1987. Charpy impact is measured according to ISO 179-1982/2/A on sheets compression moulded according to specification BS EN ISO 1872-2:1997. High Load Melt Index (HLMI) is a commonly used measure, which like MFR gives an indication of melt viscosity and hence molecular weight. It is determined by a melt indexer in terms of the melt output (g/10 minutes) under a given high load (21.6 kg) through a standard die orifice. In this application HLMI is measured according to ASTM D 1238 condition F, 21.6 kg at 190° C.

Dynamic storage modulus G' is formally defined as the storage modulus measured at a loss modulus (G") of 5 kPa. It is essentially the modulus of the melt measured "in phase" with the imposed oscillation in a dynamic test, and can be considered to quantify the elasticity of the melt. The steady state compliance ($J_s^o$) is a viscoelastic property of polymers. Methods for measuring $J_s^o$, and a discussion of its utility, can be found in a number of text books (see for example Chapters 2 and 10 of "Melt Rheology and its Role in Plastics Processing, Theory and Applications", by John M. Dealy and Kurt F. Wissbrun, published by Van Nostrand Reinhold, New York, 1990). $J_s^o$ is recognised as a useful property for polymer characterisation, and has been found to be independent of a polymer's average molecular weight but strongly affected by its molecular weight distribution, particularly by the fraction of very high molecular weight polymer present. Measurement of $J_s^o$ or some associated melt viscoelastic property is a far more sensitive method for characterising polymers for subtle differences in molecular weight distribution than are dilute solution measurements. However $J_s^o$ is difficult to measure directly for high molecular weight polyethylenes, and therefore an indirect method is used: it can be related to the storage modulus. (G'), measured in a dynamic test at low frequency (ω), by the relationship $$G'(\omega) = J_s^o [G''(\omega)]^2 \text{ for } \omega \to 0$$

where G" is the loss modulus, also measured at low frequency. In practice therefore, it is possible to measure G' at a low reference value of G", and to use this parameter as an indication of the fraction of very high molecular weight polymer present. The method for measuring G' is described in the Examples below.

In a second aspect the invention provides a homopolymer of ethylene which has a polydispersity $M_W/M_n$ of 16 or less, and and wherein the width of its molecular weight distribution at half the peak height is at least 1.6. The width of the molecular weight distribution is measured on a logarithmic scale.

Preferably the polydispersity $M_W/W_n$ is between 7 and 16. Number average molecular weight $M_n$ like $M_W$ is measured by GPC according to NAMAS method MT/GPC/02. At such relatively low polydispersities we have found that the homopolymers of the invention have a distinctive molecular weight distribution which can be expressed mathematically in the above manner. It is believed that this may at least partly account for some of the novel properties recited below.

Preferably the annealed density/molecular weight relationship is defined by the equation $D > 1105.5 M_W^{-0.0116}$. The Charpy Impact/HLMI relationship is preferably defined by the equation $I > 37.0 H^{-0.42}$, more preferably $I > 38.8 H^{-0.42}$.

Whilst polyethylene homopolymers are known which have properties defined by at least one of the above relationships, none has properties defined by both the density and Charpy Impact relationships. This unique combination of properties makes the polyethylene of the invention particularly suitable for a number of applications. For example, the improved density: melt mass-flow rate (MFR) performance (MFR being inversely proportional to molecular weight) of the compounds of the invention means that for a given MS it is possible to produce articles such as bottles or drums with a higher rigidity: weight ratio. This is particularly advantageous for the production of fast-cycling thin-walled bottles. The higher impact strength: MFR ratio is advantageous for drum or large container applications either to improve the impact strength of a container for a given weight, or to reduce the weight for a given impact strength. Thus the compounds of the invention enable containers to be made with reduced weight whilst maintaining both rigidity and impact strength.

It is also preferred that the homopolymer has an MFR drop on compounding of 20% or less when the HLMI is less than 10. By "MFR drop on compounding" is meant the difference between the Melt Flow Ratio of compounded pellets of the homopolymer and the MFR of the powder before compounding. The MFR of polyethylene generally drops upon compounding: the smaller the drop, the smaller the change in processing and viscosity properties upon compounding from powder into pellets. Thus the relatively small MFR drop experienced by the homopolymers of the invention upon compounding is advantageous as it indicates that the they can be compounded with minimal changes in properties. Melt mass-flow rate of the polymers is measured to ISO 1133:1997—Part 7. The values quoted for MFR in this specification are in dg/min.

Preferably the homopolymer also has a relationship of die swell S (at shear rate 15/s and 190° C.) to HLMI H defined by the equation $S<10\log_{10}H+30$, preferably $S<10\log_{10}H+29$, and more preferably $S<10\log_{10}H+28$. It is preferred also that the homopolymer has a polydispersity ($M_w/M_n$) of less than 30.

Preferred homopolymers also contain vinyl end-groups. Generally the vinyl content is greater than 0.3 per 1000 carbons (0.3/1000C), and preferably greater than 0.5/1000C. The number of vinyls per 1000C is determined by pressing a film of the polymer at 150° C., and obtaining a spectrum at 2 cm$^{-1}$ resolution. The vinyl concentration is determined from the 909 cm$^{-1}$ waveband according to the formula vinyl content/1000C=(14. A$_{909}$)/d.t.E where A$_{909}$=absorption at 909 cm$^{-1}$, d=density, t=film thickness, E=molar absorptivity of vinyl group.

A further aspect of the invention provides a film of a polymer of ethylene, which film has a density of at least 957 kg/m$^3$;

a Dart Impact of at least 130 g; and a polydispersity of less than 12.

The term "film" in this context means a blown film having a thickness of 100 μm or less. The film is preferably a homopolymer of ethylene. Dart Impact is a well-known test in the art, and effectively gives a measure of the force required to push a hole through a taut film. Details of the test are given in the Examples below. Preferably the Dart Impact is at least 140 g, and more preferably at least 150 g.

The polymers of the invention may be conveniently produced using a polymerisation catalyst comprising a compound of the Formula B:

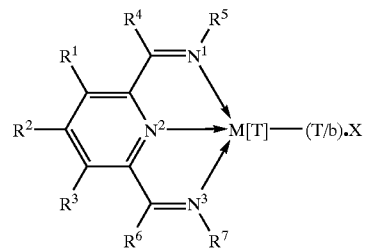

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents.

The atom or group represented by X in the compound of Formula B are preferably selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate.

It is preferred that in addition to (1) the compound of Formula B, the catalyst additionally incorporates (2) an activating quantity of an activator compound, preferably an organoaluminium compound or a hydrocarbylboron compound. Suitable organoaluminium compounds include trialkylaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, H$^+$(OEt$_2$) [(bis-3,5-trifluoromethyl)phenyl]borate, trityltetra(pentafluorophenyl)borate and tris(pentafluorophenyl)boron.

In the preparation of the preferred catalysts for making the polymers of the present invention, the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe, Co, Mn or Ru metal atom in the compound of Formula A.

The preferred polymerisation catalyst for use in the present invention preferably additionally comprises (3) a neutral Lewis base. Neutral Lewis bases are well known in the art of Ziegler-Natta catalyst polymerisation technology. Examples of classes of neutral Lewis bases suitably employed in the present invention are unsaturated hydrocarbons, for example, alkenes or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2) and (3) in an inert atmosphere (e.g. dry nitrogen) or in vacuo. If it is desired to use the catalyst on a support material (see below), this can be achieved, for example, by preforming the catalyst system comprising components (1), (2) and (3) and impregnating the support material preferably with a solution thereon or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The following are examples of nitrogen-containing transition metal complexes (1) which may be used as catalysts to make the polymers of the invention:

2,6-diacetylpyridinebis(2,6-diisopropylanil)FeCl$_2$
2,6-diacetylpyridine(2,6-diisopropylanil)MnCl$_2$
2,6-diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,4,6-trimethylanil)FeCl$_2$
2,6-diacetylpyridinebis(2,6-dimethylanil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine.FeCl$_2$.

The catalysts may contain a mixture of compounds such as, for example, a mixture of 2,6-diacetylpyridinebis(2,6-diisopropylanil)FeCl$_2$ complex and 2,6-diacetylpyridinebis(2,4,6-trimethylanil)FeCl$_2$ complex, or a mixture of 2,6-diacetylpyridine(2,6-diisopropylanil)CoCl$_2$ and 2,6-diacetylpyridinebis(2,4,6-trimethylanil)FeCl$_2$. In addition to said one or more defined transition metal compounds, the catalysts of the present invention can also include one or more other types of transition metal compounds or catalysts, for example, transition metal compounds of the type used in conventional Ziegler-Natta catalyst systems, metallocene-based catalysts, or heat activated supported chromium oxide catalysts (eg Phillips-type catalyst).

The catalysts of the present invention can be unsupported or supported on a support material, for example, silica, alumina, or zirconia, or on a polymer or prepolymer, for example polyethylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for producing homopolymer of ethylene which has:
  an annealed density D/weight average molecular weight M$_W$ relationship defined by the equation equation D>1104.5M$^{w-0.0116}$
  and a Charpy Impact I/High Load Melt Index H relationship defined by the equation I>35.0H$^{-0.4}$
which process comprises contacting the ethylene under polymerisation conditions with a polymerisation catalyst comprising (1) a compound having the Formula B as defined above and optionally (2) an activating quantity of an activator compound comprising a Lewis acid capable of activating the catalyst for olefin polymerisation.

The invention also encompasses a homopolymer of ethylene having
- an annealed density D/molecular weight M relationship defined by the equation equation $D > 1104.5 M^{-0.0116}$
- and a Charpy Impact I/High Load Melt Index H relationship defined by the equation $I > 35.0 H^{-0.4}$
- which polymer is obtainable by the above process.

A further aspect of the invention provides a process for making a film of a polymer of ethylene, which process comprises forming a polymer of ethylene which has:
- an annealed density D/weight average molecular weight $M_W$ relationship defined by the equation equation $D > 1104.5 M_W^{-0.016}$
- and a Charpy Impact I/High Load Melt Index H relationship defined by the equation $I > 35.0 H^{-0.4}$
- by a process comprising contacting the ethylene under polymerisation conditions with a polymerisation catalyst comprising (1) a compound having the B as defined above and optionally (2) an activating quantity of an activator compound comprising a Lewis acid capable of activating the catalyst for olefin polymerisation, and then blowing the resultant polymer into a film.

In a preferred process, the film comprises an ethylene homopolymer.

The compound (1) and optionally activator (2) may be contacted with the olefin to be polymerised in the form of a single catalyst system, or they may be added to the reactor separately.

The polymerisation conditions employed in the process of the invention can be, for example, solution phase, slurry phase or gas phase. If desired, the catalyst can be used to polymerise the olefin under high pressure/high temperature process conditions wherein the polymeric material forms as a melt in supercritical ethylene. Preferably the polymerisation is conducted under gas phase fluidised bed conditions. Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene.

Slurry phase polymerisation conditions or gas phase polymerisation conditions are particularly useful for the production of high density grades of polyethylene. In these processes the polymerisation conditions can be batch, continuous or semi-continuous. In the slurry phase process and the gas phase process, the catalyst is generally fed to the polymerisation zone in the form of a particulate solid. In the case of compound (1), this solid may be an undiluted solid catalyst system formed from a nitrogen-containing complex and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymerisation is supported on a support material. Most preferably the catalyst system is supported on a support material prior to its introduction into the polymerisation zone. Suitable support materials are, for example, silica, alumina, zirconia, talc, kieselguhr, or magnesia Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

The preferred polymerisation process of the present invention provides polymers at remarkably high productivity (based on the amount of polymer produced per unit weight of nitrogen-containing transition metal complex employed in the catalyst system). This means that relatively very small quantities of catalyst are consumed in commercial processes using the process of the present invention. It also means that when the process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of catalyst in the produced polymer can be very small. Experiments carried out with the preferred transition metal catalyst utilised in the present invention show that, for example, polymerisation of ethylene under slurry polymerisation conditions can provide a particulate polyethylene product containing catalyst so diluted by the produced polyethylene that the concentration of transition metal therein falls to, for example, 1 ppm or less wherein "ppm" is defined as parts by weight of transition metal per million parts by weight of polymer. Thus a preferred polyethylene homopolymer or polyethylene film according to the present invention has a transition metal content of, for example, in the range of 1–0.0001 ppm, preferably 1–0.001 ppm.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the preferred embodiment of the gas phase polymerisation process of the present invention, the gas phase polymerisation conditions are preferably gas phase fluidised bed polymerisation conditions.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (ie, the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

In use, the polymers of the invention are conventionally compounded into pellets. Additionally or alternatively, additives may be incorporated into the polymers, such as antioxidants or neutralisers. In addition to being blown into films, the polymers are particularly suitable for making a variety of moulded or extruded articles. Thus the invention also includes within its scope a polymer as defined above in the form of pellets or a film or a moulded or extruded article. Such articles include pipes, and containers such as bottles or drums.

BRIEF DESCRIPTION OF THE DRAWINGS

The present invention is illustrated in the following Examples, with reference to the accompanying graphs.

DESCRIPTION OF PREFERRED EMBODIMENTS

Figure 1:
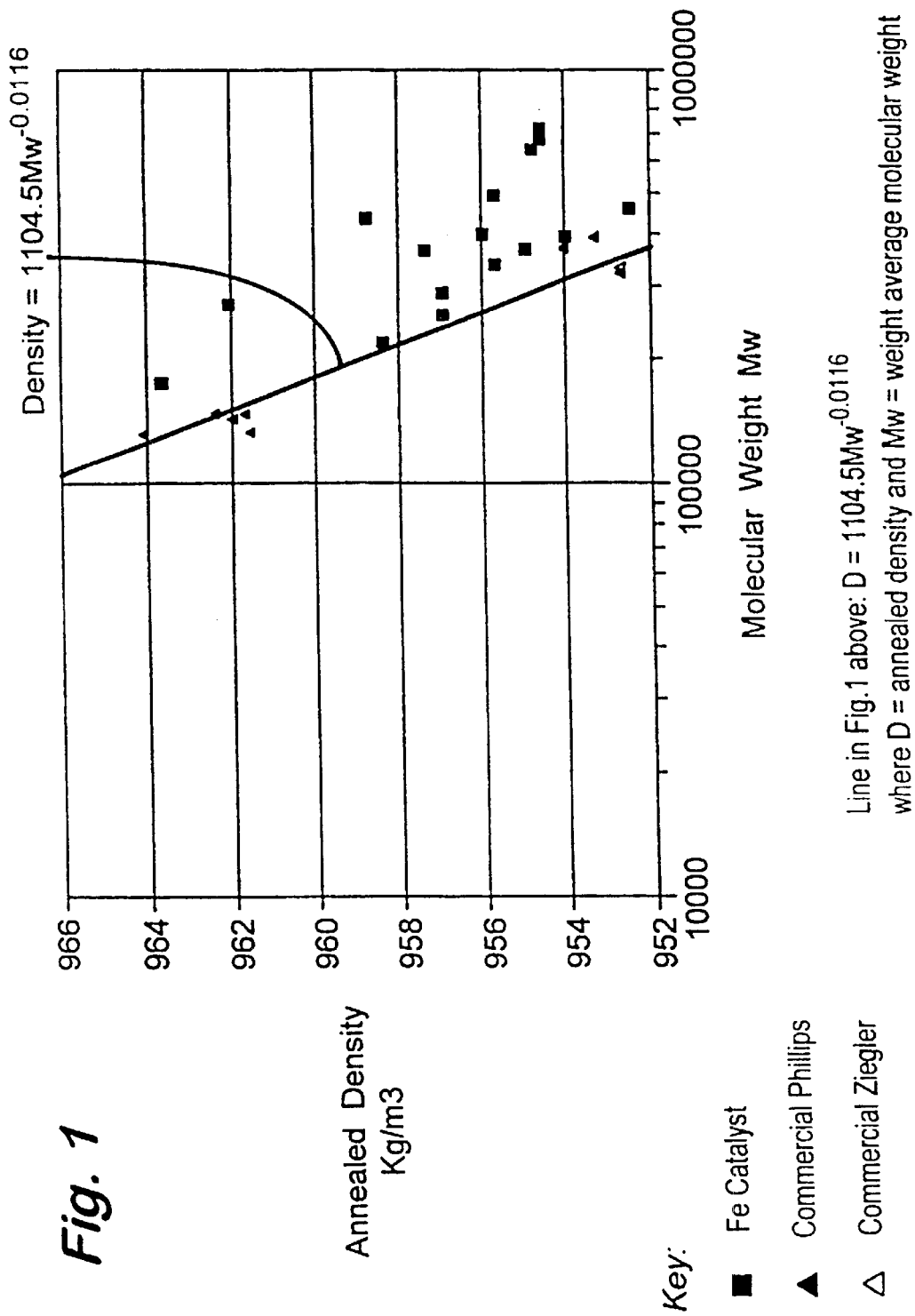
FIG. 1 shows the relationship between annealed density and weight average molecular weight for both the polymers of the invention and some commercial polymers, and shows also the line defined by the present invention; polymers within the invention are to the right of this line (as well as being above the line in FIG. 2).

In the Examples below, Example 1 corresponds to Example 9, Example 2 to Example 27, and Example 6 to Example 27.2 in GB 9805336.6 (12.03.98); Examples 3 and 7 correspond to Example 33 in GB 9806661.6 (27.03.98); and Example 4 to Example 37.1 in GE 9809598.7 (07.05.98).

EXAMPLE 1

1.1 Preparation of 2,6-Diacetylpyridinebis(2,4,6-trimethylanil)

To a solution of 2,6-diacetylpyridine (0.54 g; 3.31 mmol) in absolute ethanol (20 ml) was added 2,4,6-trimethylaniline (1.23 g; 2.5 eq.). After the addition of 2 drops of acetic acid (glacial) the solution was refluxed overnight. Upon cooling to room temperature the product crystallised from ethanol. The product was filtered, washed with cold ethanol and dried in a vacuum oven (50° C.) overnight. The yield was 60% of theoretical. $^1$H NMR(CDCl$_3$): 8.50, 7.95, 6.94, (m, 7H, ArH, pyrH), 2.33 (s, 6H, N=CCH$_3$), 2.28 (s, 6H, CCH$_3$), 2.05 (s, 12H, CCH$_3$). Mass spectrum: m/z 397 [M]$^+$.

1.2 Preparation of 2,6-Diacetylpyridinebis(2,4,6-trimethylanil)FeCl$_2$

FeCl$_2$ (0.15 g; 1.18 mmol) was dissolved in hot n-butanol (20 ml) at 80° C. A suspension of 2,6-diacetylpyridinebis (2,4,6-trimethylaniline(0.5 g; 1.18 mmol) in n-butanol was added dropwise at 80° C. The reaction mixture turned blue. After stirring at 80° C. for 15 minutes the reaction was allowed to cool down to room temperature. The reaction volume was reduced to a few ml and diethyl ether was added to precipitate the product as a blue powder, which was subsequently washed three times with 10 ml diethyl ether. The yield was 64% of theoretical.

Mass spectrum: m/z 523 [M]$^+$, 488 [M-Cl]$^+$, 453 [M-Cl$_2$]$^+$.

1.3 Preparation of 2,6-Diacetylpyridinebis(2,4,6 trimethyl anil)iron Dichloride Supported on MAO/silica All operations were conducted under nitrogen unless specified. Silica (256.62g of grade ES70X supplied by Crosfield), calcined at 200° C. under flowing nitrogen, was placed in a 2 L round bottomed flask. Toluene (900 ml) was added to the silica followed by methyl aluminoxane (441 ml, 1.5M in toluene supplied by Witco). The MAO was allowed to react with the silica at room temperature for 10 minutes at which point the temperature was raised to 80° C. and the slurry was mixed occasionally by manually shaking the flask. The temperature was maintained between 80–100° C. for a period of 2 hours.

2,6-diacetylpyridinebis(2,4,6 trimethyl anil)iron dichloride (3.48 g) was slurried in toluene (50 ml) and added to the MAO/silica slurry at 80° C. A further aliquot of toluene (20 ml) was used to ensure that all of the Fe complex was transferred to the MAO/silica. The Fe/MAO/silica was then heated at 80° C., with occasional shaking, for 1.5 hours and the solid allowed to settle. The clear supernatant solution was decanted from the flask and the catalyst partially dried under vacuum at 80° C. for 30 minutes and then left at room temperature for 16 hours. Drying of the catalyst was then continued, at 80° C. under vacuum for a further 5 hours, until a dry free flowing powder resulted and no more solvent could be detected coming off the support.

1.4–1.11: Pilot Scale Polymerisations (Slurry)

A 93 litre Phillips continuous polymerisation loop reactor was used for the polymerisations. Ethylene, isobutane diluent, hydrogen and the catalyst prepared in Example 1.3 above were metered into the reactor to maintain the reaction conditions as detailed in Table 1 below. The reactor was operated at a polyethylene throughput of approximately 7.5 kg/hour. Polymer molecular weight was controlled by variation of hydrogen addition rate.

TABLE 1

| Reaction conditions | pilot scale conditions | | | | | | | |
|---|---|---|---|---|---|---|---|---|
| | 1.4 | 1.5 | 1.6 | 1.7 | 1.8 | 1.9 | 1.10 | 1.11 |
| Temperature (° C.) | 80 | 80 | 80 | 80 | 80 | 80 | 80 | 80 |
| Catalyst Productivity (g/g) | 4495 | 4841 | 5089 | 3763 | 4750 | 5555 | 5880 | 6250 |
| Solids (wt %) | 24 | 24 | 25 | 24 | 25 | 21.5 | 25.8 | 24.0 |
| Ethylene (vol %) | 16 | 13.5 | 15 | 8.5 | 11.4 | 16 | 13.2 | 13 |
| Isobutane (litres/hour) | 22.9 | 22.6 | 23.0 | 24.4 | 24.0 | 23.6 | 22.6 | 22.5 |
| H$_2$ (ml/min, 600 psig) | 30–35 | 50 | 100 | 100 | 90 | 60 | 85 | 140 |
| Residence time (hours) | 1.6 | 1.6 | 1.6 | 1.6 | 1.6 | 1.7 | 1.6 | 15 |
| Product: | | | | | | | | |
| HLMI (21.6 kg: g/10 mins) | 2.0 | 3.0 | 16.3 | 35.9 | 6.6 | 3.3 | 7.7 | 28.7 |
| MI (21.6 kg: g/10 mins) | — | 0.04 | 0.23 | 0.52 | — | — | 0.1 | 0.45 |
| Annealed density (kg/m$^3$) | 956.4 | 958.3 | 962.1 | 963.7 | 958.5 | 960.1 | 959.8 | 963.3 |

Note that densities of Examples 1.6 to 1.8 are of compounded product

Samples of the products of Examples 1.4 to 1.7 were compounded into pellets prior to evaluation of their physical properties. A twin screw ZSK53 extruder was employed at 200° C. and output rate of 100 kg/hour. During pelletisation an antioxidant was added to give 400 ppm Irganox 1076 and 1600 ppm Irgafos 168 in compounded pellet. The product of Example 1.8 was also compounded: the powder extracted from the polymerisation reactor was stabilised with 1000 ppm of process antioxidant Irgafos PEPQ, 1000 ppm of a long term antioxidant Irganox 1010 and 1000 ppm of a neutralizer (calcium stearate). The blend of powder and additives was compounded in a twin screw extruder type Werner 53 equipped with two 53 mm diameter screws with a length/diameter ratio of 48. The temperature profile along the screw was between 220° C. and 240° C.

EXAMPLE 2

Preparation of 2,6Diacetylpyridinebis(2,4,6 trimethyl anil)iron Dichloride Supported on MAO/silica 2,6-diacetylpyridinebis(2,4,6-trimethylanil)$FeCl_2$ was prepared as described in Example 1. Silica (1.38 g ES70, supplied by Crosfield), which had been heated under flowing nitrogen at 700° C., was placed in a Schlenk tube and toluene (10 ml) was added.

To a solution of 2,6-diacetylpyridinebis(2,4,6-trimethylanil)$FeCl_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixture was maintained at 40° C., with regular stirring, for 30 minutes before the toluene was removed, at 40° C., under vacuum to yield a free flowing powder. Analysis of the solid gave 16.9% w/w Al and 0.144% w/w Fe.

EXAMPLE 3

Preparation of 2,6-Diacetylpyridinebis(2,4.6 trimethyl anil)iron Dichloride Supported on MAO/silica All the following operations were conducted under a nitrogen atmosphere unless stated. Silica (Crosfield grade ES70X) was heated under flowing nitrogen at 250° for 16 hours. A sample of this silica (2.5 g) was placed in a Schlenk tube and had 12.1 ml of 1.78M methylaluminoxane, MAO (supplied by Witco) added to it to form a slurry. The slurry was heated for 4 hours at 50° C. before being left for 10 days at room temperature. The supernatant liquid above the silica was removed and the silica/MAO washed three times with toluene (3×10 ml) at room temperature, removing the supernatant solution each time. (2,6-diacetylpyridinebis(2,4,6 trimethyl anil)iron dichloride (0.101 g) (prepared as described in Example 1) was slurried in toluene (20 ml), at room temperature, and added to the silica/MAO. The mixture was occasionally shaken over a 1 hour period. The supernatant solution was removed and the silica/MAO/Fe complex was washed with toluene until the filtrate was colourless. The solid was dried under vacuum at 50° C.

EXAMPLE 4

Preparation of 2,6-Diacetylpyridinebis(2,4,6 trimethyl anil) iron Dichloride Supported on MAO/silica Methyl aluminoxane (24 ml of 1.78M in toluene, supplied by Witco) was added to silica (1 g of grade ES70X supplied by Crosfield) which had been heated under flowing nitrogen at 250° C. The silica/MAO was heated at 80° C. for 1 hour before being washed toluene (5×10 ml aliquots). 2,6-diacetylpyridinebis(2,4,6 trimethyl anil)iron dichloride (73 mg) was slurried in toluene and transferred to the silica/MAO/toluene and left to react for 2 hours with occasional mixing. The silica/MAO/Fe complex was then washed with toluene (3×10 ml aliquots) at room temperature, and with hexane (2×10 ml aliquots) at room temperature to remove the toluene, before finally being washed with hexane at 80° C. (3×10 ml aliquots). The produced supported catalyst solid was dried under vacuum at room temperature.

EXAMPLE 5

Preparation of 2,6-Diacetylpyridinebis(2,4,6 trimethyl anil)iron Dichloride Supported on MAO/silica 2,6-diacetylpyridinebis(2,4,6 trimethyl anil)iron dichloride (34 mg, 0.065 mmol) was slurried in dry toluene (5 ml) and to it was added a toluene solution of MAO (4.3 ml of 1.5M, 6.45 mmol). The dark blue suspension immediately turned orange/brown as the Fe complex dissolved. The solution was warmed to 50° C. to ensure all the complex dissolved, and was then added to ES70X silica (2.5 g) which had been previously calcined at 200° C. in flowing nitrogen. The resulting orange slurry was shaken thoroughly and placed in a water bath at 50° C. for 1 hour with occasional shaking. On standing the orange coloured silica settled to the bottom leaving a colourless supernatant. The solvent was subsequently removed on a vacuum line at room temperature until fluidisation had ceased, to leave a free flowing pale orange powder. Calculated Composition 6.0% Al, 0.12% Fe Bench Scale Polymerisations

EXAMPLE 6

Gas Phase

The reagents used in this Example were: hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich).

A 3 litre reactor was baked out under flowing nitrogen for at least 1 hour at 77–85° C. before powdered sodium chloride (300 g, predried under vacuum, 160° C., >4 hours) was added. The sodium chloride was used as a fluidisable/stirrable start-up charge powder for the gas phase polymerisation. Trimethyl aluminium (3 ml, 2M in hexanes) was added to the reactor and was boxed in nitrogen. The alkyl aluminium was allowed to scavenge for poisons in the reactor for between ½–1 hour before being vented using 4×4 bar nitrogen purges. The gas phase composition to be used for the polymerisation was introduced into the reactor and preheated to 77° C. prior to injection of the catalyst composition. The catalyst prepared in Example 2 above (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/2.5 L methanol) and finally with water/ethanol (4:1 v/v). The polymer was dried under vacuum, at 40° C., for 16 hours. The polymerisation was carried out at a temperature of 80° C. and at an ethylene pressure of 8 bars.

EXAMPLE 7

Gas Phase

A 3 litre reactor was baked out under flowing nitrogen for at least 1 hour at 77° C. before sodium chloride (300 g, <1 mm diameter particles, predried under vacuum, 160° C., >4 hours) was added. The sodium chloride was employed merely as a standard "charge powder" for the gas phase polymerisation reactor. Trimethyl aluminium (3 ml, 2M in hexanes, supplied by Aldrich) was added to the reactor which was then closed. The alkyl aluminium was allowed to scavenge for poisons in the reactor for ½ hour before being vented by successive pressurising and purging the reactor with 4 bar of nitrogen. Ethylene (Grade 3.5, supplied by Air Products) was added to the reactor to give a pressure of 8 bar, at 77° C., prior to catalyst injection. The supported catalyst (0.215 g) prepared as described in Example 3 above was injected into the reactor under nitrogen and the temperature then adjusted to 80° C. The polymerisation was allowed to continue for 5 hours before being terminated by purging the ethylene from the reactor, using nitrogen, and reducing the temperature to below 30° C. The polymer was washed with water to remove the sodium chloride, then with acidified methanol (50 ml HCV2.5 litres methanol) and finally with water/ethanol (4:1 v/v). The polymer was dried under vacuum, at 40° C., for 16 hours. 161 g of dried polymer was produced.

EXAMPLE 8

Slurry

A 2.3 litre reactor equipped with a stirrer and jacketed for temperature control was heated under dry nitrogen at 110° C. for 1 hour. It was then cooled to 85° C., and a triisobutyl aluminium solution in dry hexane injected under nitrogen. The reactor was then charged with 1 litre of dry isobutane. The stirred reactor contents were pressurised to 600 psig by addition of dry ethylene, with the temperature maintained at 85° C.

The catalyst (Example 4 for 8.1–8.4, Example 5 for 8.5) was injected into the reactor under nitrogen, and the injection line purged with approximately 50 ml of isobutane. Reaction was then controlled at 600 psig by continuous ethylene addition, and conversion monitored from ethylene consumption. The polymerisation was conducted for the time specified in the Table below, at which point ethylene addition was stopped and the reactor vented to atmospheric pressure, prior to polymer recovery and stabilisation. The polymer was stabilised by addition of a dilute acetone solution of Irganox 1076 to give 0.15% additive in polymer. Reaction conditions, yield and activity are given in the Table below.

TABLE 2 bench scale reaction conditions

| Ex | Catalyst Weight g | Cocat. (1M)/ml | Temp ° C. | Time mins | Yield g | Prodty g/g | Activity g/g/hr |
|---|---|---|---|---|---|---|---|
| 6 | 0.211 | TMA/6 | 80 | 60 | 38 | 180 | 180 |
| 7 | 0.215 | none | 80 | 300 | 161 | 748 | 150 |
| 8.1 | 0.11 | TIBA/6 | 80 | 37 | 535 | 4865 | 7885 |
| 8.2 | 0.10 | TIBA/3 | 80 | 35 | 530 | 5300 | 9085 |
| 8.3 | 0.103 | TIBA/3 | 90 | 60 | 505 | 4900 | 4900 |
| 8.4 | 0.108 | TIBA/3 | 100 | 60 | 180 | 1670 | 1670 |
| 8.5 | 0.094 | TIBA/3 | 82 | 38 | 525 | 5585 | 8818 |

EXAMPLE 9

Gas Phase

All the following operations were conducted under a nitrogen atmosphere unless stated. A solution of methylaluminoxane (168 mmol) as a 10% wt solution in toluene, supplied by Witco, was added to a suspension of 2,6-diacetylpyridinebis (2,4,6-trimethylanil) $FeCl_2$ (2.76 mmol) prepared as in Example 1.2 above, and the mixture shaken. This solution was then added to the ES70X silica (55 g, calcined at 250° C. for 7 hours under a nitrogen purge) and the resultant slurry mixed intermittently at 70° C. for one hour. The volatile components of the resultant material were then removed under reduced pressure at 70° C. to yield the catalyst as a free flowing powder.

Polymerisation

The catalyst prepared above was used to polymerize ethylene. The polymerization was conducted in a continuous fluidised bed reactor of 15 cm diameter. Ethylene, hydrogen and aluminum alkyl were fed into the reactor: starting with a seed-bed of polyethylene powder (approx. 1000 g), catalyst was injected into the reactor and the polymerization carried out to increase the mass of the bed to approximately 3.5 kg. Polymerisation and product withdrawal was continued to yield a product substantially free of the starting bed. Process conditions for the polymerization are given in the Table below.

| Example | Aluminum Alkyl | $H_2$ [bar] | Ethylene [bar] | Al residue ppm | Si residue ppm |
|---|---|---|---|---|---|
| 9 | TMA | 0.8 | 8 | 48 | 188 |

The polymer of Example 9 was compounded as follows: the powder extracted from the polymerization reactor was stabilized with 1000 ppm of a long term antioxidant Irganox 1010 and 1000 ppm of a neutralizer (calcium stearate). The blend of powder and additives was compounded in a twin screw extruder type Werner 53 equipped with two 53 mm diameter screws with a length/diameter ratio of 48. The temperature profile along the screw was between 220° C. and 240° C.

Properties of Polymers of above Examples

Various properties of the polymers made in the above Examples were evaluated. The GPC parameters (molecular weight distribution/polydispersity, Mw, Mn) were measured according to NAMAS method MT/GPC/02. Of particular interest for pipe and moulding applications are properties such as annealed density, Melt Flow Rate (MFR), die swell and Charpy Impact. They are determined as follows:

Charpy Impact Measurement

Sheets are compression moulded according to specification BS EN ISO 1872-2:1997. The test method used is ISO 179-1982/2/A.

Melt Mass-Flow Rate (MFR)

Melt Mass-Flow Rate of the materials is measured to ISO 1133:1997—condition 7. The value quoted is MFR in dg/min.

Die Swell

Die Swell is determined on solidified extrudate taken from a Rosand RH7-2 twin bore capillary rheometer. Polymer powder or pellet is introduced into one of the rheometer barrels, which is pre-heated to 190° C. After consolidation by tamping, the polymer is allowed to melt for a period of 4 minutes, consolidated further by tamping, then allowed to condition for a further 2 minutes before testing. The piston is then introduced to the barrel and is driven into the molten polymer at constant speed. This causes the molten polymer to extrude through a capillary die of fixed dimensions at a constant.apparent wall shear rate, given by $$\text{Shear Rate} = (8.V.D^2)/d^3$$

where V denotes piston speed, D denotes diameter of the barrel (15 mm) and d denotes diameter of the capillary die. The die dimensions used are either 1 mm diameter with 16 mm length, or 2 mm diameter with 32 mm length. All dies have 180 degree (included) entrance angle. For the purposes of the invention, die swell is considered to be that measured using a 2 mm diameter die.

Extrudate samples of length around 40 mm are collected (using tweezers to pinch and remove the extrudate from the die), and allowed to cool evenly while suspended in air. The samples must be free from air bubbles and distortion. The diameter of each solidified extrudate sample is measured at two perpendicular cross-sections, about 10 mm from the bottom end of the sample, using a micrometer, and averaged to give a value for the sample. The mean value of diameter measured on 5 samples is then calculated, from which Die Swell is calculated according to the equation $$\text{Die Swell} = 100(d_m - d)/d$$

where $d_m$ is the mean diameter of the extrudate samples, and d is the diameter of the die. The value quoted is Die Swell in %, measured at a fixed apparent shear rate of 15 reciprocal seconds.

Annealed Density

This is measured to specification ISO 1872-1:1993 using test method ISO 1183:1987.

Vinyl Content/1000C

The vinyl concent is determined from the 909 $cm^{-1}$ waveband according to the formula:

$$\text{vinyl content}/1000C = (14. A_{909})/d.t.E$$

where A=absorption, d=density, t=film thickness, E=molar absorptivity of vinyl group.

% MFR Drop on Compounding

Melt mass-flow rate (MFR) of the polymers is measured to ISO 1133:1997—Part 7. The MFR is determined for the powder and the subsequently compounded pellet, the percentage drop from powder to pellet determined.

Storage Modulus

Storage Modulus G' is defined as the storage modulus measured at a loss modulus (G") of 5 kPa. The procedure for measuring G' is as follows:

Samples for dynamic rheometry are prepared by compression moulding sheet (nominally 1–2 mm thickness) using an electrically heated hydraulic press. The starting powder or pellet is placed between the pre-heated platens of the press (200° C.) and allowed to heat for 1 minute before being pressed for 2 minutes. The heating is switched off, and the press water-cooled to ambient temperature before the moulding is released.

Dynamic frequency scans are carried out using a rotational rheometer (Rheometrics ARES-2KFRTN1-FCO-STD) equipped with 25 mm diameter parallel plates enclosed in an environmental chamber. The environmental chamber is heated using nitrogen gas to avoid excessive sample degradation during testing. A 25 mm diameter disk is stamped from moulded sheet and placed between the pre-heated rheometer plates, which are then closed in such a way as to avoid the generation of excessive normal forces. The sample is trimmed and the oven closed to establish a testing temperature of 190° C. A frequency. scan is then performed at 10% applied strain over the range 100 rad/s to 0.01 rad/s.

The storage modulus (G') and the loss modulus (G") are then calculated at each testing frequency using standard equations [Draft International Standard ISO/DIS 6721/10]. G' is then plotted against G", and the value of G' at G"=5 kPa is quoted. The units of G' are kPa.

Molecular Weight Distribution (MWD)

The MWD of the polymers was determined from gel permeation chromatography (more precisely size exclusion chromatography) according to NAMAS method MT/GPC/02. The weight average molecular weight, $M_W$, and its ratio, $M_W/M_n$, to the number average molecular weight were measured by this method. In addition, the shape of the distribution was characterised by the half-width which is defined as the width of the MWD (Dlog($M_W$)) at half the peak height, H. The schematic diagram below illustrates this.

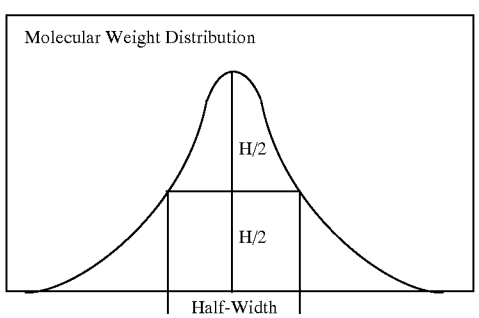

TABLE 3 properties of polymers

| Ex. | HLMI | $M_w$ | $M_w/M_n$ | MWD Half Width | Density kg/m³ | Charpy Impact kJ/m² | Die Swell 15/s, 2 mm die % | Vinyl content/ 1000 C. | MFR drop % | Storage Modulus kPa |
|---|---|---|---|---|---|---|---|---|---|---|
| 1.4 | 2.0 | 490000 | 8.9 | 1.73 | 956.4 | 33.3 | 27.2 | | 7.9 | 2.45 |
| 1.5 | 3.0 | 363100 | 15.6 | 1.81 | 958.3 | 27.3 | 28.4 | | 9.4 | 2.43 |
| 1.6 | 16.3 | | | | | | | | | |
| 1.6a | 9.8 | 226200 | 14.7 | 1.78 | | 15.1 | 32.1 | | | 2.54 |
| 1.7 | 35.9 | | | | | | | | | |
| 1.4* | 1.8 | — | | | 957.6 | 44.9/40.1# | — | | | |
| 1.5* | 3.0 | — | | | 959.1 | 34.4/35.3# | — | | | |
| 1.6* | 12 | — | | | 962.1 | 16.5 | 35.8 | | | 2.42 |
| 1.7* | 28 | — | | | 963.7 | 10.3 | 38.8 | | | 2.39 |
| 1.9* | 2.8 | 327060 | 13.9 | 1.88 | 959.7 | 29.6 | 26.5 | 0.65 | 15.2 | 2.91 |
| 1.10 | 7.7 | | | | 959.8 | — | — | 0.61 | | |
| 1.11* | 25.0 | 189000 | 12.9 | 1.74 | 963.8 | 12.3 | 38.8+ | 0.7 | | 2.46 |
| 6 | | 223000 | | | | | | | | |
| 7 | 0.7 | 499000 | | | 951.2 | 47.9 | 17 (estimate) | | | |
| 8.1 | 5.0 | 289770 | 13 | 1.72 | 957.0 | 24.6 | 34.5 | | | 2.53 |
| 8.2 | 2.0 | 403815 | 13 | 1.77 | 954.0 | 31.7 | 30.5 | | | 2.57 |
| 8.3 | 3.7 | 333425 | 8.9 | 1.68 | 955.7 | 25.4 | 31.7 | | | 2.48 |
| 8.4 | 13.4 | 217595 | | | 958.4 | 14.5 | 37.9 | | | 2.56 |
| 8.5 | 1.84 | 432400 | 10.5 | 1.82 | 958.8 | 31.0 | — | | | |
| 9 | 10.2 | 213000 | | | 957 | | | | | |

*= after compounding into pellets
= two measurements of Charpy Impact made
+= 1 mm die Compounding of Examples 1.4 and 1.5 employed a ZSK53 twinscrew extruder operated with a temperature profile ranging from 200–240° C. A set screw speed of 250rpm was used and output rate adjusted to maintain a 70% torque rating. This corresponded to 65–75 kg/hour throughput. During pelletisation 1% weight of an antioxidant concentrate was added to give a stabiliser content of 500 ppm Irganox 1010; 300 ppm Irganox 1076 and 1200 ppm Irgafos 168.

The homopolymers of the present invention are advantageous because whilst there are known homopolymers of polyethylene which have some of the properties of those of the invention, the combination of these properties in a single homopolymer is novel. The advantages of this novel combination of properties have previously been mentioned, and include the ability to be able to make containers with reduced weight whilst maintaining both rigidity and impact strength.

Examples of known homopolymers of polyethylene are given in Table 4 below; all are derived from Phillips chromium catalysts except for Hostalen GM6255, which is a Ziegler product. All tests were performed on compounded pellets.

TABLE 4 comparative examples: properties of known polymers

| Name | HLMI g/10 min | $M_w$ | $M_w/M_n$ | MWD Half Width | Density kg/m³ | Charpy Impact kJ/m² | Die Swell at 15/s % | Storage Modulus kPa |
|---|---|---|---|---|---|---|---|---|
| Rigidex HM5550EP | 4.0 | 269000 | 11.7 | 1.55 | | 18.1 | 41.7 | 3.75 |
| Rigidex HM5420XP | 2.1 | 360000 | 15 | 1.53 | 954.5 | 24.0 | 43.5 | 3.80 |
| Rigidex HD6007EA | 44.9 | 130000 | 6.9 | 1.37 | | 7.4 | 64.0+ | 3.26 |
| Rigidex HD6007XA | 49.4 | 126000 | 8 | 1.32 | appr. 964 | | 66.0+ | 3.33 |
| Hostalen GM6255 | 2.2 | 334000 | 8.5 | 1.52 | 953.2 | 23.9 | 34.7 | 3:57 |

+1 mm die (others all 2 mm die)

Figure 2:
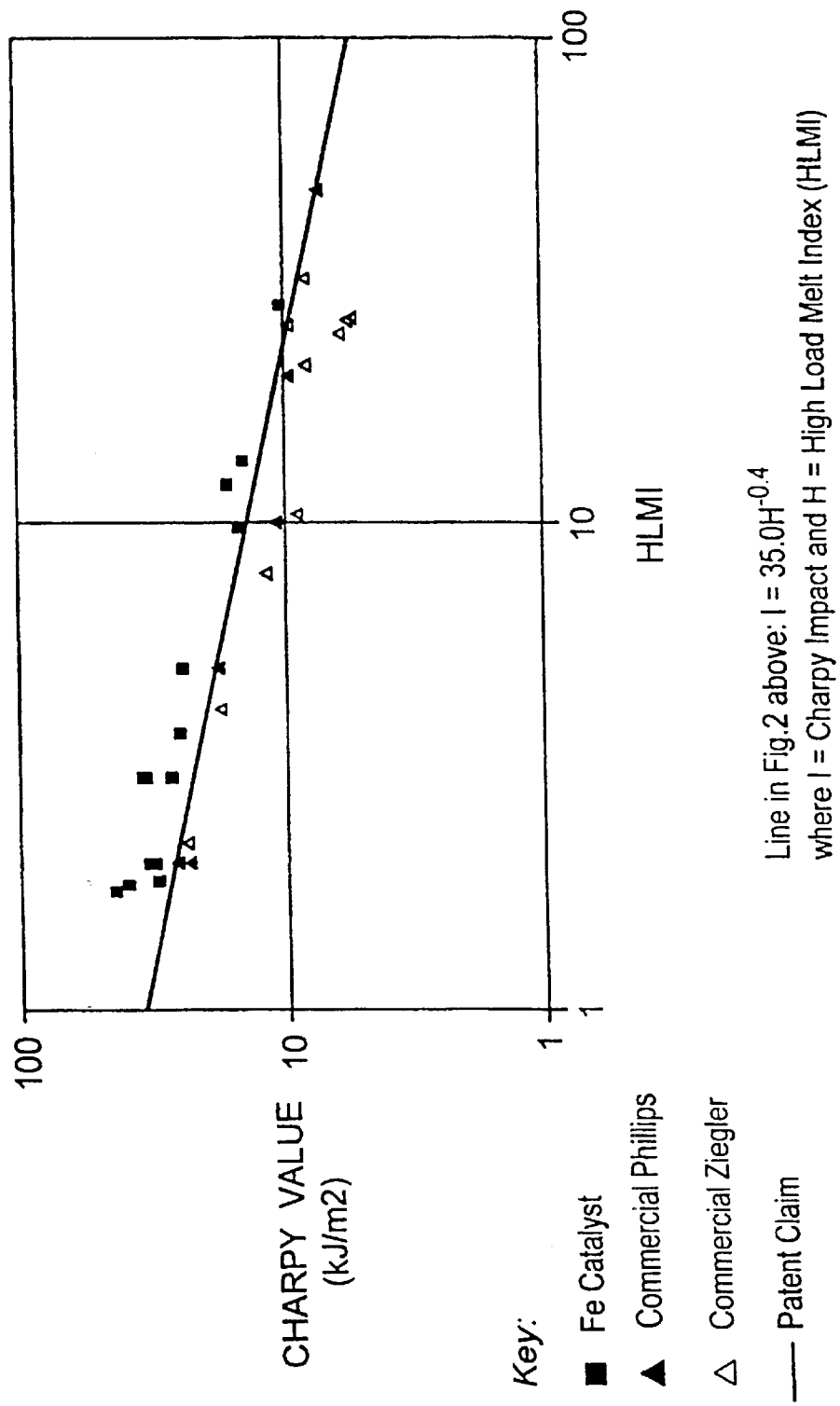
FIG. 2 shows the relationship between Charpy Impact and HLMI for both the polymers of the invention and some commercial polymers, and shows also the line defined by the present invention; polymers within the invention are above this line (as well as being to the right of the line in FIG. 1).
Figure 3:
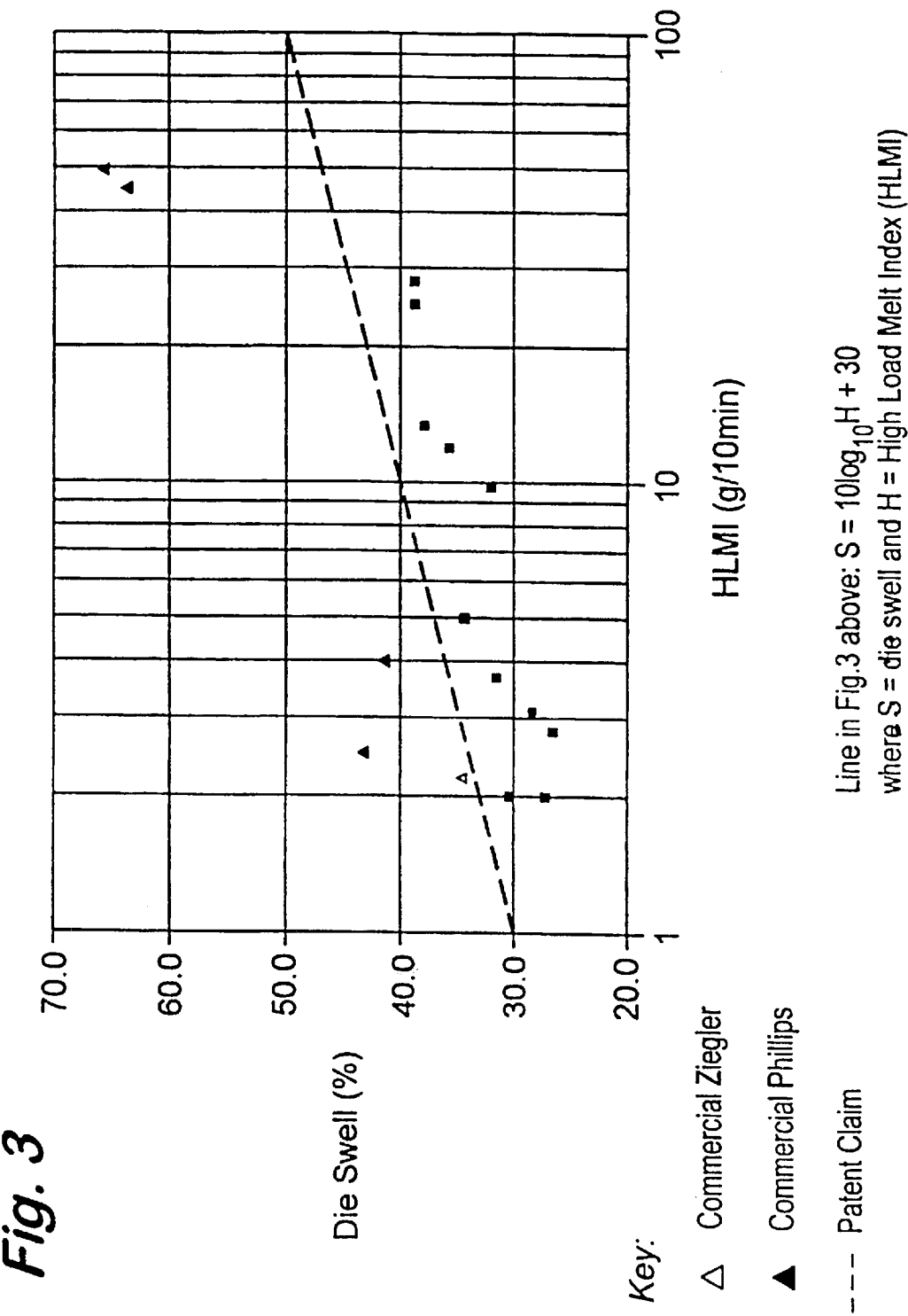
FIG. 3 shows the relationship between die swell and HLMI for both the polymers of the invention and some commercial polymers, and shows also the line defined by preferred polymers of the present invention; such preferred polymers are below this line (as well as being to the right of the line in FIG. 1 and above the line in FIG. 2).
Figure 4:
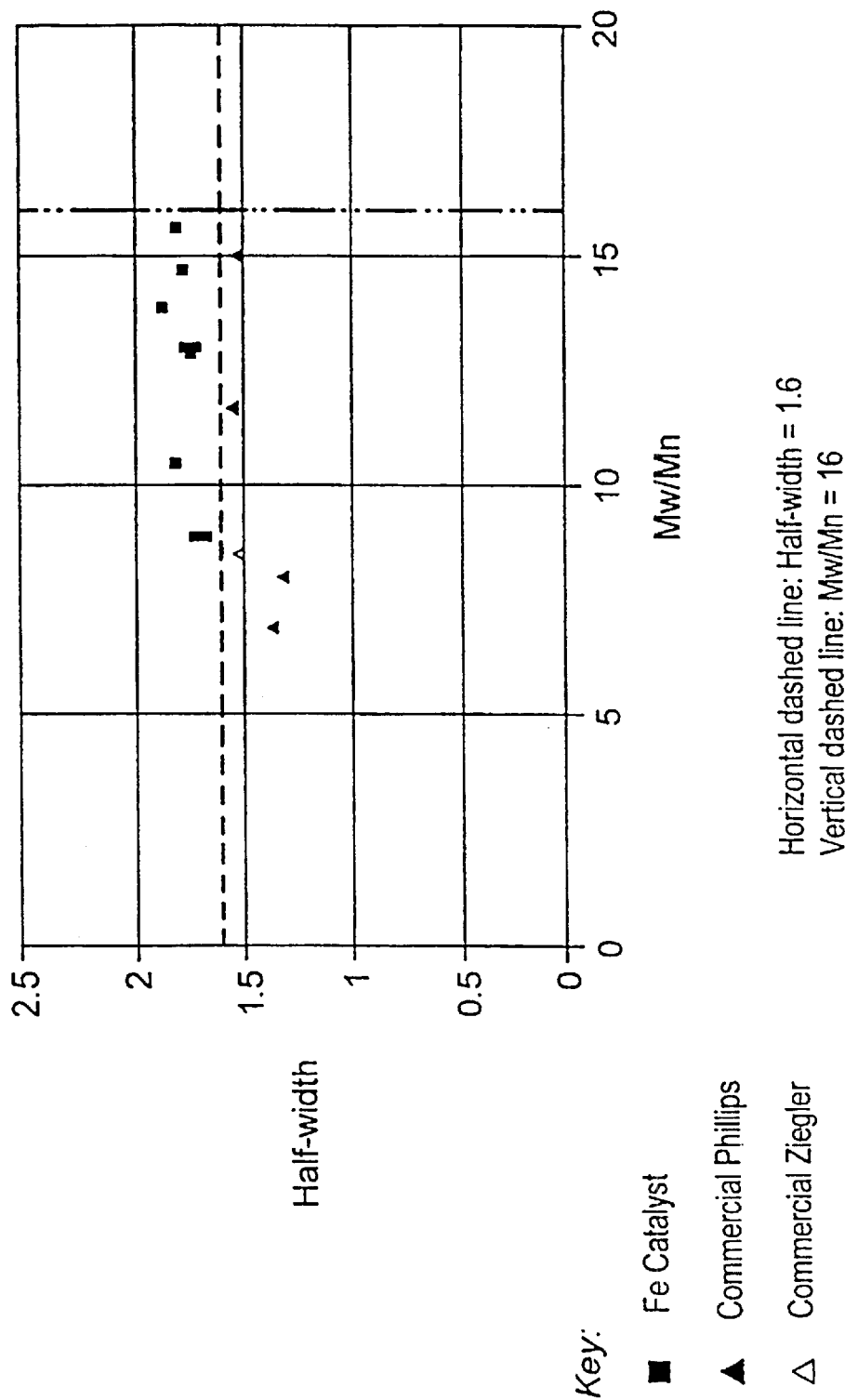
FIG. 4 shows the relationship between the half-width of the molecular weight distribution and the polydispersity $M_w/M_n$ where the latter is 16 or below. Preferred polymers of the invention have a half-width of at least 1.6.

The relationships between annealed density and molecular weight, Charpy Impact and HLMI, and Die Swell and HLMI are shown graphically in FIGS. 1–3 respectively. Data for half-width is shown in FIG. 4. These graphs show points representing the data in Tables 3 and 4 above, together with lines representing the relationships defined in the invention.

Film Production

The pellets produced from Example 1.8 and 9 were converted into a film. They were extruded on a blown film extruder Collin 180/600 type, equipped with a grooved barrel and a 45 mm diameter screw with a L/D of 25. The die diameter was 70 mm and die gap 0.8 mm. The output was 9 kg/h and the temperature profile along the screw from 195° C. to 220° C. The film thickness was 15 microns, and the film produced with a neck height between 5 and 8×D (D is the die diameter) with a Blow Up Ratio of 3:1.

The mechanical properties of the films produced were then measured. Dart Impact is determined according to ASTM D1709-85; Elmendorf tear strength is determined according to ASTM D1922-89. In addition to mechanical properties the Film Appearance Rating (FAR), which is a measurement of the gels and fish-eyes content, is given to each film sample. A positive value (i.e. above zero) is considered a good rating.

TABLE 5 properties of blown film

|  | Example 1.8* |  | Example 9 | Hizex 7000F |
|---|---|---|---|---|
| $M_w$ | 222000 |  | 214000 | 209000 |
| $M_n$ | 21000 |  | 22000 | 10000 |
| $M_w/M_n$ (polydispersity) | 10.6 |  | 9.7 | 21 |
| Density of initial polymer (kg/m³) | 958.5 |  | 959.4 | 950.0 |
| Dart Impact (g) | 205 | 86 | 147 | 320 |
| Film Appearance Rating (FAR) | +20 | +10 | +30 | +40 |
| Elmendorf Tear Strength (g/25 µm) |  |  |  |  |
| Machine Direction | 56 | 19 | 56 | 28 |
| Transverse Direction | 83 | 207 | 465 | 96 |

* Left column is data for film blown with neck height of 8×diameter, right hand column is for film blown with neck height 5×diameter.

The table above shows the properties of the film blown from the polymers of Examples 1.8 and 9, compared with a commercially available film; Hizex 7000F available from Mitsui. It should be noted that because the Examples of the invention are experimental products, one would expect them to have inferior properties to commercial products which have been optimised. In fact Example 1.8 exhibits excellent dart drop impact at 200 g for a nominal 15 microns film, which is exceptional in view of the high density of the product (958.5 kg/m³) associated with the narrow Molecular Weight Distribution (a polydispersity index (ratio $M_w/M_n$) of 10.6). In addition, the FAR of both films produced were excellent at +20 and +30, which is outstanding for a lab scale product.

What is claimed is:

1. Homopolymer of ethylene which has:
   an annealed density D/weight average molecular weight $M_W$ relationship defined by the equation $D > 1104.5 M_W^{-0.0116}$ where D is expressed in kg/m³; and
   either a Charpy Impact I/High Load Melt Index H relationship defined by the equation $I > 35.0 H^{-0.4}$, where I is expressed in kJ/m² and H in g/10 min,
   or a dynamic storage modulus G' of 2.9 or less.

2. Homopolymer of ethylene according to claim 1 which has a polydispersity $M_w/M_n$ of less than 30.

3. Homopolymer of ethylene which has a polydispersity $M_w/M_n$ of 16 or less, and wherein the width of its molecular weight distribution at half the peak height is at least 1.6.

4. Homopolymer of ethylene according to claim 2 or 3 wherein the polydispersity $M_w/M_n$ is between 7 and 16.

5. Homopolymer of ethylene according to claim 1 or 3 which has an annealed density D/molecular weight $M_w$ relationship defined by the equation $D > 1105.5 M_w^{-0.0116}$.

6. Homopolymer of ethylene according to claim 1 or 3 having a Charpy Impact I/HLMI H relationship defined by the equation $I > 37.0 H^{-0.42}$.

7. Homopolymer of ethylene according to claim 6 wherein the Charpy Impact I/HLMI relationship is defined by the equation $I > 38.8 H^{-0.42}$.

8. Homopolymer of ethylene according to claim 1 or 3 which has a relationship of die swell S (at shear rate 15/s and 190° C.) to HLMI H defined by the equation $S < 10 \log_{10} H + 30$.

9. Homopolymer of ethylene according to claim 8 wherein the relationship of die swell S to HLMI H is defined by the equation $S < 10 \log_{10} H + 29$.

10. Homopolymer of ethylene according to claim 8 wherein the relationship of die swell S to HLMI H is defined by the equation $S < 10 \log_{10} H + 28$.

11. Homopolymer of ethylene according to claim 1 or 3 having an HLMI of 10 or less and a melt mass-flow rate drop upon compounding of no more than 20%.

12. Homopolymer of ethylene according to claim 1 or 3 wherein the vinyl content is greater than 0.3 per 1000 carbons (0.3/1000C).

13. Homopolymer of ethylene according to claim 12 wherein the vinyl content is greater than 0.5/1000C.

14. Homopolymer of ethylene according to claim 1 or 3 in the form of pellets, a film or a moulded or extruded article.

15. Homopolymer of ethylene according to claim 14 in the form of a pipe or container.

16. Homopolymer of ethylene according to claim 1 or 3 additionally comprising antioxidants and/or neutralisers.

17. A film of a polymer of ethylene, which film has
   a density of at least 957 kg/m³;
   a Dart Impact of at least 130 g, as determined according to ASTM D1709-85; and
   a polydispersity of less than 12.

18. Film according to claim 17 wherein the Dart Impact is at least 140 g.

19. Film according to claim 17 wherein the Dart Impact is at least 150 g.

* * * * *

UNITED STATES PATENT AND TRADEMARK OFFICE
CERTIFICATE OF CORRECTION

PATENT NO.    : 6,455,660 B1
DATED         : September 24, 2002
INVENTOR(S)   : Edward Quentin Clutton et al.

It is certified that error appears in the above-identified patent and that said Letters Patent is hereby corrected as shown below:

<u>Column 22,</u>
Line 28, "S<10log,$_{10}$H+28" should read -- S<10log$_{10}$H+28 --.

Signed and Sealed this

Sixth Day of May, 2003

JAMES E. ROGAN
*Director of the United States Patent and Trademark Office*